United States Patent
Stinchcomb et al.

(10) Patent No.: US 6,569,449 B1
(45) Date of Patent: May 27, 2003

(54) TRANSDERMAL DELIVERY OF OPIOID ANTAGONIST PRODRUGS

(75) Inventors: Audra L. Stinchcomb, Latham, NY (US); Peter W. Swaan, Columbus, OH (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/711,640

(22) Filed: Nov. 13, 2000

(51) Int. Cl.$^7$ ................................................ A61F 13/00
(52) U.S. Cl. ........................ 424/449; 424/443; 424/448
(58) Field of Search ..................... 424/449, 443, 424/448

(56) References Cited

U.S. PATENT DOCUMENTS

| | | | |
|---|---|---|---|
| 4,573,995 A | 3/1986 | Chen et al. | |
| 4,626,539 A | 12/1986 | Aungst et al. | |
| 4,668,685 A | 5/1987 | Shami | |
| 4,673,679 A | * 6/1987 | Aungst et al. | 514/282 |
| 4,806,341 A | 2/1989 | Chien et al. | |
| 4,935,428 A | 6/1990 | Lewis | |
| 5,096,715 A | 3/1992 | Sinclair | |
| 5,149,538 A | 9/1992 | Granger et al. | |
| 5,239,714 A | 8/1993 | Lee et al. | |
| 5,816,260 A | * 10/1998 | Kallman et al. | 128/898 |
| 5,817,665 A | 10/1998 | Dante | |
| 5,834,480 A | * 11/1998 | Elkhoury | 514/289 |
| 5,908,846 A | * 6/1999 | Bundgaard et al. | 514/282 |
| 5,972,954 A | 10/1999 | Foss et al. | |

* cited by examiner

Primary Examiner—Thurman K. Page
Assistant Examiner—Isis Ghali
(74) Attorney, Agent, or Firm—McDermott, Will & Emery

(57) ABSTRACT

A composition, a method and an apparatus for transdermally delivering an effective amount of opioid antagonists derived from prodrugs for treatment of eating disorders, narcotic dependence and alcoholism. In addition, the present invention relates to a composition, a method and an apparatus for transdermally delivering an effective amount of an opioid and opioid antagonist derived from an opioid agonist and one of an opioid antagonist and a prodrug for treatment of pain.

22 Claims, 2 Drawing Sheets

TRANSDERMAL DELIVERY OF OPIOID ANTAGONIST PRODRUGS

BACKGROUND OF THE INVENTION

1. Technical Field

The present invention relates to a composition, a method and an apparatus for transdermally delivering an effective amount of opioid antagonists derived from prodrugs for treatment of eating disorders, narcotic dependence and alcoholism. Alternatively, the present invention relates to a composition, a method and an apparatus for transdermally delivering an effective amount of an opioid antagonist derived from pro-drugs and an effective amount of an opioid agonist for treatment of pain.

2. Related Art

Opioid antagonists such as Naltrexone may be used for treatment of narcotic dependence and alcoholism. Naltrexone is currently available as Naltrexone Hydrochloride in a 50-mg oral tablet (ReVia®).

There is a need to accurately deliver effective amounts of opioid antagonists such as Naltrexone in a manner that encourages voluntary compliance when such opioid antagonists are used for the treatment of narcotic dependence and alcoholism.

SUMMARY OF THE INVENTION

The present invention provides a composition, a method and an apparatus for transdermally delivering an effective amount of opioid antagonists derived from prodrugs for treatment of narcotic dependence and alcoholism. In addition, the present invention relates to a composition, a method and an apparatus for transdermally delivering an effective amount of an opioid antagonist derived from prodrugs and an effective amount of an opioid agonist for treatment of pain.

DETAILED DESCRIPTION OF THE INVENTION

Figure 1:
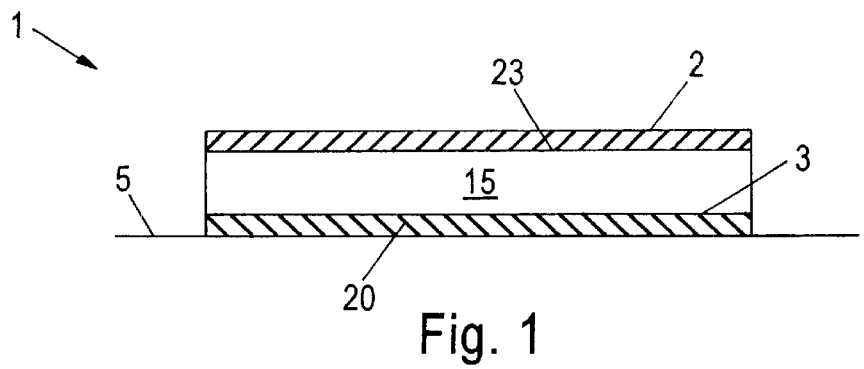
FIG. 1 depicts a front cross-sectional view of a transdermal drug delivery apparatus on a substrate, in accordance with preferred embodiments of the present invention.

The present invention relates to an apparatus, a method and a composition for transdermally delivering an effective amount of opioid antagonists derived from prodrugs for treatment of narcotic dependence and alcoholism. Hereinafter, the term "effective amount" is an optimal transdermally delivered dose of prodrug, determined by one skilled in the art, needed for treating narcotic dependence and alcoholism. Also hereinafter, the term "transdermally delivering or delivery" means applying and affixing a skin permeable prodrug to the skin, wherein the prodrug undergoes physiological hydrolysis, resulting in introducing the hydrolyzed prodrug into the systemic circulatory system of a mammal. Also, hereinafter, the term "physiological hydrolysis or physiologically hydrolyzable, or physiologically hydrolyzing" means replacement of R, or R and $R_1$ in prodrugs (I)–(X) infra with a hydrogen atom as the prodrug passes through the skin. In addition, hereinafter, the term "opioid antagonist" refers to various substances that are able to block the receptors for opiates and thus prevent the euphoric effects of, e.g. morphine and alcohol. Furthermore, hereinafter the term "prodrug" refers to a drug that has been chemically modified by substitution of an R or $R_1$ group as in the prodrugs (I)–(X) infra.

The apparatus for transdermal delivery comprises: a prodrug permeable adhesive layer having a first surface and a second surface on a substrate; a prodrug layer, having an exposed surface, operatively attached to a first surface of the adhesive layer; and a prodrug impermeable polymer film on the exposed surface of the prodrug layer and on a second surface of the adhesive layer. Alternatively, the prodrug layer and an opioid may be operatively attached to the first surface of the adhesive layer. The substrate may be mammalian such as human skin. The prodrug may be a derivative of naltrexone, nalbuphine, nalorphine, naloxone, nalmefene, cyclazocine, levallorphan, cyclorphan, oxilorphan, and pentazocine, described infra which are permeable through the dosage form and also permeable to the skin to which the dosage form is applied. Alternatively, opioid(s) which are permeable through the adhesive layer and are also permeable through the skin may be operatively attached to the adhesive layer. By the term "opioid" is meant any natural or synthetic opioid analgesic or other narcotic analgesic or mixtures thereof. Some examples of suitable opioids useful according to this invention are alfentanil, allylprodine, alphaprodine, anileridine, benzylmorphine, bezitramide, buprenorphine, butorphanol, clonitazene, codeine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazionl, metazocine, methadone, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, phenoperidine, piminodine, piritramide, proheptazine, promedol, properidine, propiram, propoxyphene, sufentanil, tilidine, fentanyl and pharmaceutically acceptable salts thereof and mixtures thereof. The most preferred opioids are fentanyl, buprenorphine, and pharmaceutically acceptable salts thereof. Alternatively, morphine derivatives that are permeable to the skin in analgetically effective amounts such as those disclosed by Bundgaard et al. in 1999, in U.S. Pat. No. 5,908,846, herein incorporated by reference, may be operatively attached to the first surface 17 of the adhesive layer 20.

FIG. 1 illustrates a front cross-sectional view of a transdermal drug delivery apparatus 1 on a substrate 5, in accordance with preferred embodiments of the present invention. The substrate 5 includes substrate material such as mammalian or human skin. The transdermal delivery apparatus 1 comprises: a prodrug permeable adhesive layer 20, having a surface 3, formed on the substrate 5, wherein the prodrug permeable adhesive layer 20 includes adhesive materials; a prodrug layer 15 formed on the surface 3 of the prodrug permeable adhesive layer 20, wherein the prodrug layer 15 has an exposed surface 23, and wherein the prodrug layer 15 comprises prodrug materials that diffuse into the prodrug permeable adhesive layer 20, and a polymer film 2, formed on the exposed surface 23 of the prodrug layer 15, wherein the polymer film may be made from materials that are impermeable to the prodrug. The adhesive layer 20 may be prepared from polymers and copolymers may be selected from the group consisting of, but not limited to, butyl acrylate, ethyl acrylate, ethyl hexyl acrylate, vinylacetate/ethylene acrylate and mixtures thereof. The prodrug layer 15 includes inter alia prodrug materials derived from an effective amount of opioid antagonists such as naltrexone, nalbuphine, nalorphine, naloxone, nalmefene, cyclazocine, levallorphan, cyclorphan, oxilorphan, and pentazocine, or combinations thereof. Alternatively, the prodrug layer 15 may include a permeation enhancer material in addition to the prodrug material, wherein the permeation enhancer material and the prodrug material are mixed to form a solution, suspension, gel or matrix having the effective amount of prodrug. The device may be any of the general types known in the art including adhesive matrix and reservoir type transdermal delivery systems. The permeation enhancer material may include, but is not limited to, lauric acid, oleic acid, linoleic acid, octanol, decanol, lauryl alcohol, myristyl alcohol, myristoleyl alcohol, palmitoleyl alcohol, oleyl alcohol, linolenyl alcohol, linolyl alcohol, elaidyl alcohol, vaccenyl alcohol, petroselinyl alcohol, petroselaidyl alcohol, methyl caproate, propyl caproate, hexyl acetate, methyl heptylate, pentyl heptylate, heptyl acetate, heptyl caproate, methyl caprylate, propyl caprylate, octyl acetate, octyl butylate, methyl caprate, ethyl caprate, hexyl caprate, methyl pelargonate, butyl pelargonate, lauryl acetate, lauryl butylate, methyl laurate, ethyl laurate, isopropyl laurate, hexyl laurate, methyl myristate, ethyl myristate, isopropyl myristate, pentadecyl acetate, methyl palmitate, ethyl palmitate, isopropyl palmitate, hexadecyl acetate, methyl oleate, ethyl oleate, butyl oleate, dimethyl adipate, disopropyl adipate, disobutyl adioate, dimethylmaleate, diisopropyl malate, dibutyl malate, dihexyl maleate, ethyl alcohol and mixtures thereof. The polymer film 2 may be made from materials including polyethylene, polypropylene, ethylene/propylene copolymers, ethylene/ethylacrylate copolymers, ethylene/vinyl acetate copolymers, silicone elastomers, medical-grade polydimethylsiloxanes, neoprene rubber, polyisobutylene, chlorinated polyethylene, polyvinyl chloride, vinylchloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethyleneviny-loxyethanol copolymer; silicone copolymers, polysiloxane-polycarbonate copolymers, polysiloxane-polyethyleneoxide copolymers, polysiloxane-polymethacrylate copolymers, polysiloxane-polymethacrylate copolymers, polysiloxane-alkylene copolymers polysiloxane-ethylene copolymers, polysiloxane-alkylenesilane copolymers, polysiloxaneethyl-enesilane copolymers, cellulose polymers, methyl cellulose, ethyl cellulose, hydroxypropyl methyl cellulose, cellulose esters, polycarbonates, polytetrafluoroethylene, starches, gelatins, natural gums, synthetic gums, and combinations thereof.

Figure 2:
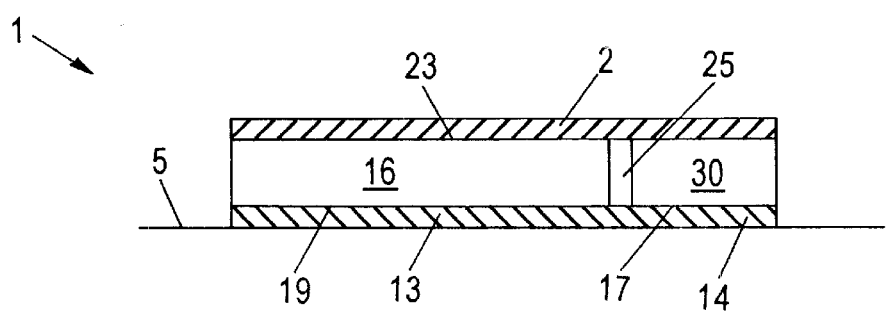
FIG. 2 depicts FIG. 1 after an impermeable barrier has been formed in the transdermal drug delivery apparatus.

FIG. 2 depicts FIG. 1 after forming a prodrug impermeable barrier 25 between the surface 3 of the prodrug permeable adhesive layer 20 and the prodrug impermeable polymer film 2. The drug impermeable barrier 25 may be made from drug impermeable materials that include polyethylene, polypropylene, ethylene/propylene copolymers, ethylene/ethylacrylate copolymers, ethylene/vinyl acetate copolymers, silicone elastomers, medical-grade polydimethylsiloxanes, neoprene rubber, polyisobutylene, chlorinated polyethylene, polyvinyl chloride, vinylchloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethyleneviny-loxyethanol copolymer; silicone copolymers, polysiloxane-polycarbonate copolymers, polysiloxane-polyethyleneoxide copolymers, polysiloxane-polymethacrylate copolymers, polysiloxane-polymethacrylate copolymers, polysiloxane-alkylene copolymers polysiloxane-ethylene copolymers, polysiloxane-alkylenesilane copolymers, polysiloxaneethyl-enesilane copolymers, cellulose polymers, methyl cellulose, ethyl cellulose, hydroxypropyl methyl cellulose, cellulose esters, polycarbonates, polytetrafluoroethylene, starches, gelatins, natural gums, synthetic gums, and combinations thereof. A prodrug layer 16 has been formed on a surface 19 of a portion 13 of the prodrug permeable adhesive 20 and a prodrug layer 30 has been formed on a surface 17 of a remaining portion 14 of the prodrug permeable adhesive layer 20. The prodrug layers 16 and 30 include inter alia prodrug materials derived from an effective amount of opioid antagonists such as naltrexone, nalbuphine, nalorphine, naloxone, nalmefene, cyclazocine, levallorphan, cyclorphan, oxilorphan, and pentazocine or combinations thereof, described infra as prodrugs. (I)–(X). Alternatively, effective amounts of opioid antagonists such as naltrexone, nalbuphine, nalorphine, naloxone, nalmefene, cyclazocine, levallorphan, cyclorphan, oxilorphan, and pentazocine or combinations thereof may be operatively attached to the first surface 17 of the adhesive layer 20. Alternatively, the prodrug layers 16 and 30 may include a mixture containing a permeation enhancer material described supra and an effective amount of the prodrug material. Alternatively, opioid(s) which, are permeable through the adhesive layer and are also permeable through the skin may be operatively attached to the first surface 17 of the adhesive layer 20. Alternatively, morphine derivatives that are permeable to the skin in analgetically effective amounts such as those disclosed by Bundgaard et al. in U.S. Pat. No. 5,908,846, supra, may be operatively attached to the first surface 17 of the adhesive layer 20.

Another embodiment of the present invention is a method comprising the step of: transdermally delivering an effective amount of an opioid antagonist selected from the group consisting of naltrexone, nalbuphine, nalorphine, naloxone, nalmefene, cyclazocine, wherein the opioid antagonist is derived from a prodrug selected from the group consisting of, but not limited to naltrexone-R (I), nalbuphine-R,R$_1$ (II), nalorphine-R,R$_1$ (III), naloxone-R (IV), nalmefene-R (V), cyclazocine-R (VI), having the, following formulas:

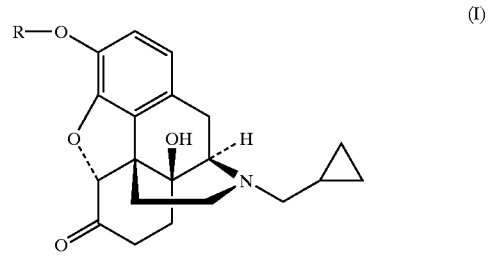

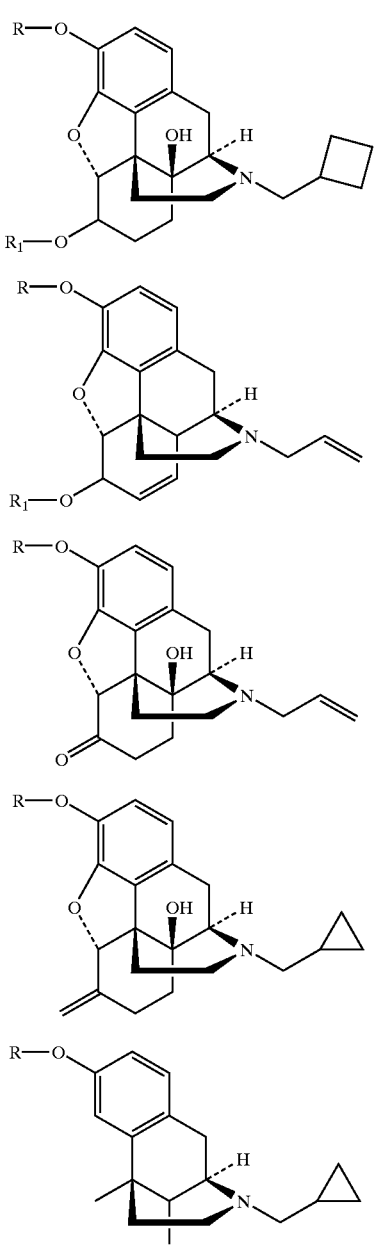

and wherein R and $R_1$ are physiologically hydrolyzable and are selected from, but not limited to, alkylcarbonyl, arylcarbonyl, alkyloxycarbonyl, aryloxycarbonyl, carbamoyl, succinyl phosphate, pivalyl and combinations thereof. When either R or $R_1$ include an alkylcarbonyl group, or when both include an alkylcarbonyl group, the alkylcarbonyl group further comprises acetyl, propionyl, valeroyl, pentanoyl, hexanoyl, heptanoyl, isobutyroyl, 2-ethylbutryoyl and 2-propylpentanoyl and combinations thereof. When either R or $R_1$ include an alkylcarbonyl group, or when both include a carbamoyl group, the carbamoyl group further comprises N,N-diethyl-amino-carbamoyl, N-butyl-amino-carbamoyl, N,N-propyl-amino-carbamoyl, N-hexyl-amino-carbamoyl, N-heptyl-amino-carbamoyl and N-octyl-amino-carbamoyl and combinations thereof.

Alternatively, the present invention is a method comprising the step of: transdermally delivering an effective amount of an opioid antagonist selected from the group consisting of levallorphan, cyclorphan, oxilorphan and pentazocine wherein substitution of a hydroxyl group in levallorphan has resulted in levallorphan-R (VII), in cyclorphan has resulted in cyclorphan-R (VIII), in oxilorphan has resulted in oxilorphan-R (IX), and in pentazocine has resulted in pentazocine-R (X), and wherein R is physiologically hydrolyzable and has been selected from, but not limited to, alkylcarbonyl, arylcarbonyl, alkyloxycarbonyl, aryloxycarbonyl, carbamoyl, succinyl phosphate, pivalyl and combinations thereof. When R includes an alkylcarbonyl group, the alkylcarbonyl group further comprises acetyl, propionyl, valeroyl, pentanoyl, hexanoyl, heptanoyl, isobutyroyl, 2-ethylbutryoyl and 2-propylpentanoyl and combinations thereof. When R includes a carbamoyl group, the carbamoyl group further comprises N,N-diethyl-amino-carbamoyl, N-butyl-amino-carbamoyl, N,N-propyl-amino-carbamoyl, N-hexyl-amino-carbamoyl, N-heptyl-amino-carbamoyl and N-octyl-amino-carbamoyl and combinations thereof.

Results

Opioid antagonists such as naltrexone do not have the essential physicochemical properties that would allow an effective dose of the opioid antagonists to cross the human skin barrier. Hereinafter the term "physicochemical property" means a property that includes both physical and chemical phenomena. The prodrugs of the present invention represented by chemical structures (I)–(VI) supra are more skin permeable and rapidly converted to their opioid antagonist analogues by physiological hydrolysis.

Figure 3:
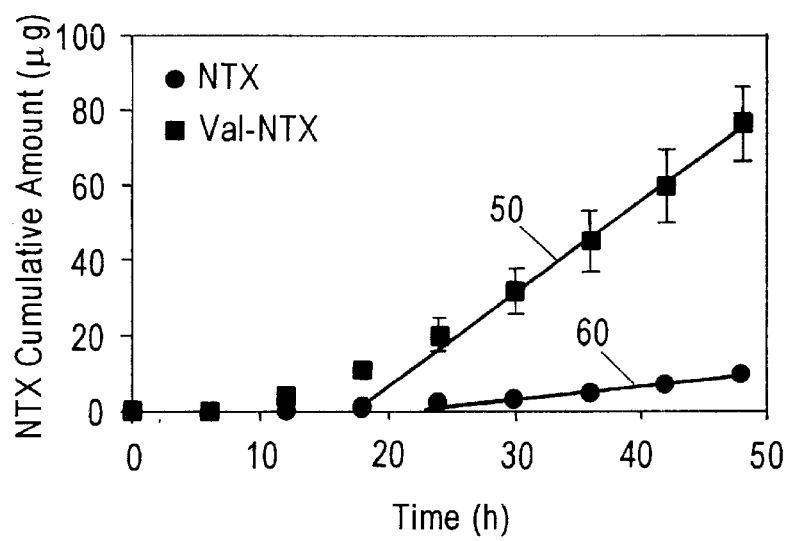
FIG. 3 is a graph showing NTX and Valeroyl-NTX accumulation over time as measured in vitro.

The effect of transdermal delivery of the prodrug of structure (I), wherein R is valeroyl (Val-NTX) is depicted in FIG. 3 and associated discussion under In Vitro Diffusion Studies in Example 1 infra. FIG. 3 depicts the accumulation in micrograms (μg) of naltrexone (NTX) in a receiver compartment of a diffusion cell when a saturated solution at 32° C. of Val-NTX 50 or NTX 60 was passed through human skin. NTX amounts were measured at 6 hour intervals for 48 hours. Further, FIG. 3 depicts about an eight-fold increase in the amount of NTX produced by physiological hydrolysis when the prodrug Val-NTX was transdermally delivered through the skin sample into the receiver compartment of the diffusion cell compared to the amount of NTX delivered when naltrexone was transdermally delivered through the skin sample. The data in FIG. 3 represent the mean±one standard deviation of three cells with naltrexone in the donor compartment and four cells with Val-NTX prodrug in the donor compartment, using human skin from one individual.

The lipophilic prodrugs such as Val-NTX and Hep-NTX provide a higher flux of naltrexone across the skin than naltrexone base (One-way ANOVA, $p<0.01$). The Hep-NTX prodrug exhibits a trend towards providing more flux enhancement than the Val-NTX prodrug, an eight-fold average increase in the flux enhancement ratio versus a four-fold average increase for Val-NTX. The flux enhancement ratios should not be limited to the 13:1 ratio in FIG. 4, but may be substantially greater. Table 1 infra lists the relative concentrations (μmol/gram skin) of NTX, wherein physiological hydrolysis of the prodrug having the chemical structure (I), supra, wherein R is valeroyl (Val-NTX) or heptanoyl (Hep-NTX) results from transdermal delivery of NTX through the skin. The mean molar percentage of regenerated naltrexone to total drug extracted from the skin was about 31–38% for Val-NTX and Hep-NTX.

TABLE 1

Relative Concentrations (μmol/gram skin) of NTX:Prodrug From In Vitro Diffusion Studies.

| Drug Treatment | NTX μmol/g skin, (%) | Prodrug μmol/g skin |
|---|---|---|
| Val-NTX | 0.651, 31 | 1.08 |
| Hep-NTX | 1.426, 38 | 2.29 |

Table 1 supra lists relative concentrations (μmol/gram skin) of NTX:prodrug from in vitro diffusion studies. Associated text in Example 1 under In Vitro Diffusion Studies describe calculation of a prodrug flux enhancement ratio (NTX flux from prodrug/NTX flux) for each subject's sample of skin tested. Since human skin exhibits wide inter-subject permeation variability, this flux enhancement ratio is a good way to compare the effect of the prodrug versus NTX, within each individual skin sample. Using the method for calculating a mean flux enhancement ratio described infra in Example 1, the mean flux enhancement ratio for the Val-NTX experiments is 4.4±1.5 (one standard deviation), and an increased mean flux enhancement ratio of 8.3±4.6 (one standard deviation) is calculated for the Hep-NTX data.

Skin esterases are quite resistant to the stresses of freezing and storing, which is why prodrug is converted in the frozen skin experiments. In fact, the enzymatic stability studies were done in previously frozen tissue samples, and a rapid enzymatic conversion rate was observed in these experiments. The rapid enzymatic conversion rate of the Val-NTX is a positive attribute for drug delivery, as the active drug would be quickly released in the body after crossing the skin.

The prodrugs' melting points were measured, as this physicochemical property is often easily related to the prodrugs' solubilities (Stinchcomb et al., *A Solubility and Related Physicochemical Property Comparison of Buprenorphine and its 3-alkyl Esters*, Pharm. Res., 12, 1526–1529 (1995). Hereinafter the term "physicochemical property" means a property that includes both physical and chemical phenomena. The downward trend in melting points as a function of increasing alkyl chain length can be seen infra in Table 2.

TABLE 2

Molecular Weights (Mw), and Melting Points (MP) of Naltrexone and its Ester Prodrugs.

| Drug | R-group | MW | MP (° C.) |
|---|---|---|---|
| NTX | —H | 341 | 166–169 |
| VAL-NTX | —CO(CH$_2$)$_3$CH$_3$ | 425 | 83–85 |
| HEP-NTX | —CO(CH$_2$)$_5$CH$_3$ | 453 | 58–60 |

Table 2 supra lists Val-NTX and Hep-NTX prodrug melting points, showing a decrease as the alkyl chain is extended, by over 100° C. in the case of the heptyl ester. The fact that the ester prodrugs exhibit lower melting points than naltrexone base strongly suggests that the added alkyl functionalities disrupt the intra-crystalline cohesion of the drug. This crystal destabilization can have a profound effect on solubilities. As expected, Table 2 supra lists the Val-NTX prodrug has a higher oil (nonpolar) solubility than the parent drug.

Table 3 infra lists inter alia Val-NTX and Hep-NTX aqueous solubilities, wherein the prodrugs exhibit much lower aqueous solubilities than naltrexone base because of the prodrug's lack of the free phenolic functional group, a group that promotes aqueous solubility through hydrogen bonding.

TABLE 3

Physicochemical Properties of Naltrexone and Its Ester Prodrugs. Experimental Values Shown with Standard Deviations Are the Means of at Least Two Determinations.

| Drug | Calculated[a] log P[b] | Experimental log P[b] | Light Mineral Oil Solubility 32° C., (mmol/L) | Phosphate Buffer Solubility pH 7.4 32° C., (mmol/L) | 1st order 32° C., pH7.4 t$_{1/2}$ (hr) |
|---|---|---|---|---|---|
| NTX | 0.36 | 0.67 ± 0.02 | 0.258 ± 0.012 | 15.2 ± 1.6 | No degradation seen in 10 days |
| Val-NTX | 1.95 | 1.77 ± 0.10 | 9.62 ± 0.024 | 0.593 ± 0.002 | 96 ± 10 |
| Hep-NTX | 3.01 | Not available | Not available | 0.180 ± 0.030 | 103 ± 17 |

[a]calculated from Daylight ® 4.51 Software
[b]log P = log octanol/water partition coefficient The octanol/water partition coefficient increased logarithmically with the addition of the valeryl chain, as seen in Table 3.

Use of Daylight® 4.51 Software enabled calculation of log P (clogP) values for Naltrexone, and ester and carbamoyl prodrugs listed infra in Table 4.

TABLE 4

Calculated LOG P (clog P) of Naltrexone and Its Ester and Carbamoyl Prodrugs.

| | MW | clogP |
|---|---|---|
| Ester-R-group | | |
| —H (NTX) | 341 | .355 |
| —COCH$_3$ | 383 | .361 |
| —COCH$_2$CH$_3$ | 397 | .890 |
| —COCH$_2$CH$_2$CH$_3$ | 411 | 1.419 |
| —CO(CH$_2$)$_3$CH$_3$ | 425 | 1.948 |
| —CO(CH$_2$)$_4$CH$_3$ | 439 | 2.477 |
| —CO(CH$_2$)$_5$CH$_3$ | 453 | 3.006 |
| —COCH$_2$CH(CH$_3$)$_2$ | 425 | 1.821 |
| —COCH(CH$_2$CH$_3$)$_2$ | 439 | 2.257 |
| —COCH(CH$_2$CH$_2$CH$_3$)$_2$ | 467 | 3.318 |
| Carbamate Ester-R-Group | | |
| —CON(CH$_2$CH$_3$)$_2$ | 440 | 1.36 |
| —CON(CH$_2$)$_3$CH$_3$ | 440 | 1.67 |
| —CON(CH$_2$CH$_2$CH$_3$)$_2$ | 468 | 2.42 |
| —CON(CH$_2$)$_5$CH$_3$ | 468 | 2.73 |
| —CON(CH$_2$)$_6$CH$_3$ | 481 | 3.26 |
| —CON(CH$_2$)$_7$CH$_3$ | 495 | 3.79 |

[a]Calculated from Daylight ® 4.51 Software.
[a]Calculated log P (clog P) = log octanol/water partition coefficient.

By using Daylight® 4.51 Software, one skilled in the art could calculate log P (clog P)=log octanol/water partition coefficient for prodrugs (I)–(X) wherein R and R$_1$ are physiologically hydrolyzable and are selected from, but not limited to, the group consisting of alkylcarbonyl, arylcarbonyl, alkyloxycarbonyl, aryloxycarbonyl and carbamoyl and combinations thereof, without the need for further experimentation. In addition, Table 3 supra lists the log octanol/water partition coefficients for Val-NTX and Hep-NTX prodrugs, wherein the log octanol/water partition coefficient is from about 1 to about 4. Based on the In Vitro Diffusion Studies described infra in Example 1, the data listed in Table 2 supra supporting the 8-fold flux enhancement ratio when the source of the naltrexone was Hep-NTX and the 4-fold flux enhancement ratio when the source of naltrexone was Val-NTX, and FIG. 3, supporting the 8-fold increased cumulative amount of naltrexone transdermally delivered through the skin, one skilled in the art could reasonably make and use the present invention to treat alcohol and narcotic dependence, according to the embodiments of the present invention.

Prodrug chemical stability to hydrolysis was monitored in pH 7.4 phosphate buffer at 32° C. The prodrugs hydrolyzed in the buffer in an apparent first-order fashion; therefore plots were made of the natural logarithm of concentration depletion as a function of time. The observed half-lives calculated using the curves from these plots are summarized infra in Table 1. The slopes of the curves, which are equal to the rate constant, were determined using linear regression analysis. None of the coefficients of determination for the lines were less than 0.95. The half-lives were calculated by dividing 0.693 by the individual rate constants. All chromatograms from the degradation experiments showed an increasing naltrexone peak as the prodrug was depleted. The prodrug hydrolysis reactions were carried out to at least four half-lives.

In Vitro Diffusion Studies

In almost all cases, the prodrugs were completely hydrolyzed on passing through the skin and appeared as naltrexone in the receiver compartment. Therefore, plots of the cumulative amounts of NTX permeated through human skin over time from saturated mineral oil solutions of either a prodrug or naltrexone base were constructed for data analysis. A representative NTX permeation profile is shown FIG. 3. Steady-state fluxes and lag times calculated using the terminal, linear regions of the curves are shown in FIGS. 3 and 4, respectively.

Figure 4:
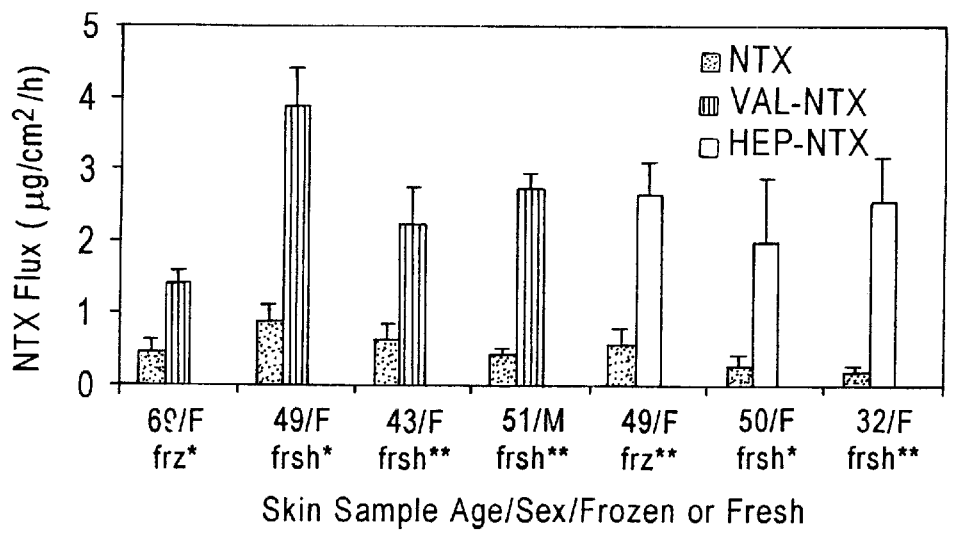
FIG. 4 is a bar graph showing the effect of age, sex or condition of skin sample (fresh or frozen) on NTX flux.
Figure 5:
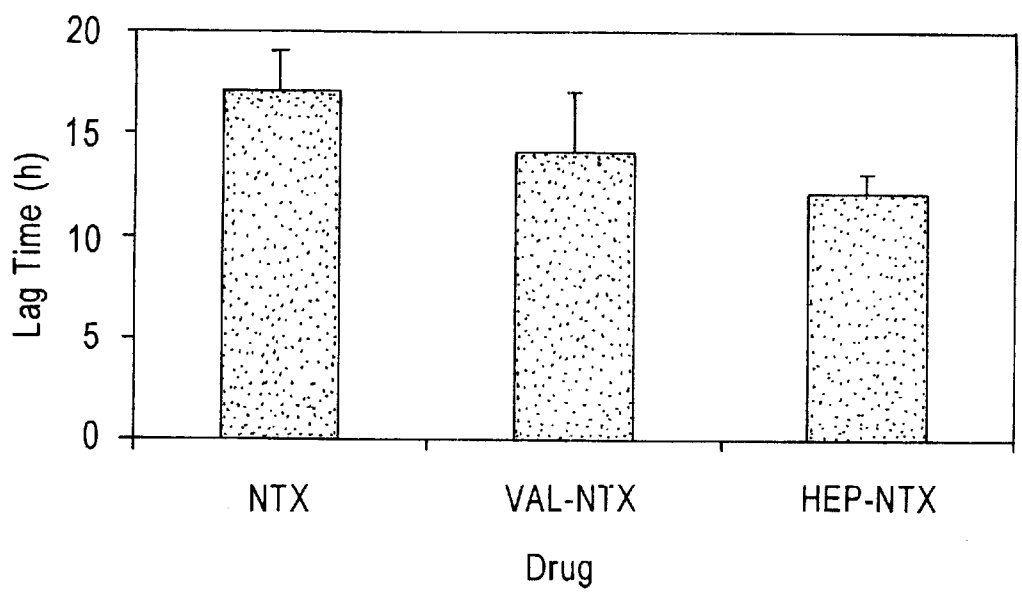
FIG. 5 is a bar graph showing the lag time in flux for NTX, Valeroyl-NTX and Hep-NTX.

"Lag times" which hereinafter mean the delay before detectable naltrexone appears in the receiver compartment of the diffusion cell due to physiological hydrolysis of Val-NTX or Hep-NTX are depicted in FIG. 4. The data represents the mean +/− one standard deviation of three cells with naltrexone in the donor compartment and four cells with saturated solutions of Val-NTX or Hep-NTX in the donor compartment, using human skin from one individual. The skin donor age, sex, and skin sample storage condition are shown for each experiment. F=female and M=male. Previously frozen skin samples (7–12 months) are indicated by frz, and samples used fresh are indicated by frsh. *Isotonic phosphate buffer, pH=7.4. **HEPES-buffered Hank's balanced salts solution.

Example 1 infra describes in vitro diffusion studies with human skin using the prodrug material (I), wherein R is a valeryl group (Val-NTX) and wherein R is a heptanoyl group (Hep-NTX), to determine the level of opioid antagonist transdermal delivery enhancement. In Example 1, Val-NTX and Hep-NTX are more skin permeable than naltrexone (NTX) and are rapidly converted to the respective opioid antagonist in the viable skin layers.

EXAMPLE 1

Naltrexone (NTX) base was purchased from Mallinckrodt Inc., St. Louis, Mo. The prodrug were synthesized directly from naltrexone base. The drugs' melting points were measured on a hot-stage melting point apparatus (Fisher-Johns, Pittsburgh, Pa.). Reagent-grade chemicals were obtained from Sigma Chemical Co. (St. Louis, Mo.).

Prodrug Synthesis

Val-NTX and Hep-NTX prodrug Material were synthesized by dissolving naltrexone base (50 mg, 0.13 mmol) in 1 ml methylene chloride and triethylamine (50 ml, 0.7 mmol). The solution was placed in an ice bath and stirred. The acid chloride (0.15 mmol) of the desired prodrug moiety, or a solution thereof in methylene chloride, was added dropwise. After addition was complete, the reaction mixture was allowed to warm up to room temperature and stirred for an additional 4 hrs. The progress of the reaction was followed with thin layer chromatography (TLC): small samples (10 ml) of the reaction mixture were spotted on silica gel plates and developed in an n-butanol:acetic acid:water (10:1:1) cosolvent system. After drying, the plates were sprayed with 10% $H_2SO_4$ in ethanol and heated at 100° C. for 5 min. NTX and its Prodrugs were detected as brown spots with typical $R_f$ values (e.g. NTX=0.4 and Val-NTX=0.6). After completion of the reaction, the methylene chloride solution was washed with 10% aqueous sodium carbonate and then with water, dried over anhydrous sodium sulfate, filtered, and reduced to a small volume on a rotary evaporator. The esters were precipitated by adding excess petroleum ether and the desired product was filtered off and dried on air. Purity was checked by reversed-phase HPLC with UV-detection (230 nm) using a water-acetonitrile gradient (0–100% acetonitrile in 20 min.) on a C18 analytical column. If the purity was less than 95%, the compounds were further purified by preparative HPLC. The final products were characterized by $^1$H-nuclear magnetic resonance spectroscopy (NMR, IBM FTNMR NR/250) and mass spectrometry. Val-NTX m/e was 425.22. Hep-NTX m/e was 453.25. Val-NTX, $^1$H NMR (DMSO-$d_6$): d 0.16–0.53 (m, 5H, cyclopropyl), 0.96 (t, 3H, $CH_3$), 1.3–3.4 (m, 20H, aliphatic), 4.85 (s, 1H, C-5) 6.31–6.62 (2d, 2H, aromatic); $C_{25}H_{31}NO_5$. Hep-NTX, $^1$H NMR (DMSO-$d_6$): d 0.19–0.47 (m, 5H, cyclopropyl), 0.91 (t, 3H, $CH_3$), 1.3–1.59 (m, 8H, aliphatic), 2.19–2.94 (m, 8H, aliphatic), 4.85 (s, 1H, C-5) 6.31–6.62 (2d, 2H, aromatic); $C_{27}H_{35}NO_5$.

The HPLC system consisted of a Waters 717 Autosampler, 501 Pumps, and a 484 Tunable UV Absorbance Detector with Millennium Chromatography Software. A reversed phase 22-cm Brownlee C-18 Spheri-5 micron column (and guard column) were used with the UV detector set at a wavelength of 215 nm. The mobile phase consisted of 0.1% trifluoroacetic acid (adjusted to pH 3 with triethylamine): acetonitrile: sodium heptane sulfonate (300 mL:700 mL:0.3 g) at a flow rate of 1.5 mL/min. One hundred microliters of sample were injected onto the column. Standard curves exhibited excellent linearity over the entire concentration range employed in the assays. The assay sensitivity was 10 ng/mL.

The prodrug materials Val-NTX and Hep-NTX were isolated from the buffer samples by solid-phase extraction (Oasis HLB, Waters Corp., Milford, Mass.). The solid-phase extraction cartridge was pretreated with one milliliter of methanol and one milliliter of water before the aqueous drug sample was run through the cartridge. After running the sample through the cartridge, the sample was washed with one milliliter of 5% methanol/water, and eluted with acetonitrile. Sample recovery was ninety-eight percent.

Octanol/Water Partition Coefficients

The octanol/water partition coefficients were determined using pH 7.4 isotonic phosphate buffer as the aqueous phase. All steps were carried out at room temperature. An appropriate amount of drug was weighed into a vial and dissolved in a known amount of octanol. An equivalent amount of buffer was then added to the vial and the phases shaken for 24 hours. The vials were left undisturbed for at least one hour after shaking. An exact volume was taken from the aqueous phase, diluted with acetonitrile, and then analyzed by HPLC. The final pH of the aqueous phase at the end of the shaking period was 7.95. Similarly, an exact volume was taken from the octanol phase, diluted with acetonitrile, and then analyzed by HPLC. Partition coefficients were calculated by determining the phase concentration ratios.

Solubilities

The solubilities of naltrexone and its esters were obtained by equilibrating large excesses of each substance with the respective vehicle, light mineral oil, or pH 7.4 isotonic phosphate buffer at 32° C. To hasten the attainment of equilibrium, each slurry was continuously shaken in a sealed container in a shaking incubation oven. Samples were taken, filtered (mineral oil:Millex FG-13, Millipore and buffer-:glass microfiber, Gelman) above 32° C., measured with respect to volume, and diluted with the appropriate amount of acetonitrile. The diluted samples were analyzed by HPLC. The initial forty percent of each filtrate was discarded to eliminate the possibility that adsorption of drug on the filter and/or the filtering apparatus might influence the solubility determination. The sampling procedure was repeated at least once for each sample. Concentration versus time plots indicated that equilibrium was obtained in less than 48 hours. Therefore, the equilibration times for all the studies were 48 hours.

Chemical Stability

Solutions of the respective drug in pH 7.4 phosphate buffer were monitored over time. The solutions were stored in sealed vials in a 32° C. incubation oven. At appropriate time intervals, samples were removed, isolated from the buffer by solid-phase extraction, and stored at 4° C. until HPLC quantitation.

In Vitro Diffusion Studies

The aim of in vitro experimentation in transdermal drug delivery is to quantitate the penetration of a drug molecule through the skin. Skin excised during abdominal reduction surgery from several patients was used for the permeation studies. Skin samples were sectioned from the excised abdominal tissue using a Padgett dermatome set to 250 μm; some skin samples were frozen at −80° C., others were used immediately. A PermeGear flow-through (In-Line, Riegelsville, Pa.) diffusion cell system was used for the permeation studies. The receiver fluid was isotonic phosphate buffer at pH 7.4 in some experiments, and in more recent experiments we switched to a HEPES-buffered Hank's balanced salts solution, in order to help preserve tissue viability. The flow rate of the receiver fluid was set at 1 ml/hr in order to help maintain sink conditions. The drugs were isolated from the receiver samples by solid-phase extraction, and stored at 4° C. until HPLC quantitation. The temperature of the diffusion cells was maintained at 32° C. with a circulating water bath. The diffusion experiment was initiated by charging the donor compartment with 0.25 ml of drug suspended (saturated solution) in light mineral oil.

The permeation data were plotted as the cumulative amount of drug collected in the receiver compartment as a function of time. The flux value for a given run was calculated from Fick's First Law of diffusion, infra:

Formula 1:

$$\frac{1}{A}\frac{(dM)}{(dt)} = J_s = P\Delta C$$

In this equation, $J_s$ is the steady-state flux in g/cm$^2$/h; A is the area of the membrane, 0.95 cm$^2$; P is the effective permeability coefficient in cm/h; and $\Delta C$ is the concentration gradient across the membrane. Since build up in the receiver cell was kept to a minimum throughout the studies, the latter is well approximated by the donor concentration.

Drug disposition in the diffusion cell skin samples was measured at the end of the 48-hour experiment. The skin sample was removed from the diffusion cell and rinsed with distilled water, in order to remove the surface formulation. Further removal of the skin surface formulation was accomplished by blotting with a paper towel, and stripping with adhesive tape applied to the surface and quickly removed two times. The treated area of the skin was cut from the skin sample and minced with a scalpel. The wet tissue weight was recorded and the sample was placed in a vial with ten milliliters of acetonitrile. The drug was extracted from the tissue by sonicating the solution for ten minutes and shaking the vial overnight. The samples were assayed by HPLC and reported as mmol of drug per gram of wet tissue weight.

What is claimed is:

1. A method for delivering an effective amount of an opioid antagonist selected from the group consisting of naltrexone, nalbuphine, nalorphine, naloxone, nalmefene, cyclazocine, levallorphan, cyclorphan, oxilorphan and pentazocine comprising transdermally administering an opioid antagonist prodrug selected from the group consisting of naltrexone-R (I), nalbuphine-R,R$_1$ (II), nalorphine-R,R$_1$ (III), naloxone-R (IV), nalmefene-R (V), cyclazocine-R (VI), levallorphan-R (VII), cyclorphan-R (VIII), oxilorphan-R (IX), and pentazocine-R (X), wherein R and R$_1$ are physiologically hydrolyzable and are independently selected from the group consisting of alkylcarbonyl, arylcarbonyl, alkyloxycarbonyl, aryloxycarbonyl, phosphate and carbamoyl.

2. The method of claim 1, wherein transdermally delivering the prodrug results in a naltrexone flux enhancement ratio (flux from prodrug:flux from naltrexone) from about 3:1 to about 13:1.

3. The method of claim 1, wherein the step of transdermally delivering further comprises applying the prodrug to an epidermal layer of human skin.

4. The method of claim 1, wherein the step of transdermally delivering further comprises applying the prodrug to an epidermal layer of animal skin.

5. The method of claim 1, wherein R and R$_1$ include an alkylcarbonyl group selected from the group consisting of acetyl, propionyl, valeroyl, pentanoyl, hexanoyl, heptanoyl, isobutyroyl, pivalyl, succinyl, 2-ethylbutryoyl and 2-propylpentanoyl and combinations thereof.

6. The method of claim 1, wherein R and R$_1$ include a carbamoyl group selected from the group consisting of N,N-diethyl-amino-carbamoyl, N-butyl-amino-carbamoyl, N,N-propyl-amino-carbamoyl, N-hexyl-amino-carbamoyl, N-heptyl-amino-carbamoyl and N-octyl-amino-carbamoyl and combinations thereof.

7. The method of claim 1, wherein the step of transdermally delivering further comprises using a prodrug having a log octanol/water partition coefficient from about 1 to about 4.

8. The method of claim 1, wherein the step of transdermally delivering further comprises substantially physiologically hydrolyzing R and $R_1$.

9. The method of claim 7, wherein the step of transdermally delivering further comprises substantially physiologically hydrolyzing R and $R_1$.

10. The method of claim 1 wherein the prodrug is naltrexone-R, and wherein R is an alkylcarbonyl group.

11. The method of claim 10 wherein the alkylcarbonyl group is valeroyl.

12. The method of claim 10, wherein the alkylcarbonyl is heptanoyl.

13. A method for enhancing the delivery of an opioid antagonist through the skin of a patient comprising topically administering to the patient a prodrug of the opioid antagonist, wherein the prodrug is selected from the group consisting of naltrexone-R (I), nalbuphine-R,$R_1$ (II), nalorphine-R,$R_1$ (Ill), naloxone-R (IV), nalmefene-R (V), cyclozocine-R (VI), levallorphan-R (VII), cyclorphan-R (VIII), oxilorphan-R (IX), and pentazocine-R (X), wherein R and $R_1$ are physiologically hydrolizable and are independently selected from the group consisting of alkylcarbonyl, arylcarbonyl, alkyloxycarbonyl, aryloxycarbonyl, phosphate and carbamoyl.

14. The method of claim 13 wherein the prodrug is naltrexone-R.

15. The method of claim 13 wherein R is an alkylcarbonyl.

16. The method of claim 14 wherein the alkylcarbonyl is valeroly.

17. The method of claim 14 wherein the alkylcarbonyl is heptanoyl.

18. A method of treating alcoholism or narcotic dependence comprising topically administering to a patient an effective amount of a prodrug of an opioid antagonist, wherein the prodrug is selected from the group consisting of naltrexone-R (I), nalbuphine-R,$R_1$ (II), nalorphine-R,$R_1$ (III), naloxone-R (IV), nalmefene-R (V), cyclozocine-R (VI), levallorphan-R (VII), cyclorphan-R (VIII), oxilorphan-R (IX), and pentazocine-R (X), wherein R and $R_1$ are physiologically hydrolizable and are independently selected from the group consisting of alkylcarbonyl, arylcarbonyl, alkyloxycarbonyl, aryloxycarbonyl, phosphate and carbamoyl and combinations thereof.

19. The method of claim 17 wherein the prodrug is naltrexone-R.

20. The method of claim 18 wherein R is an alkylcarbonyl.

21. The method of claim 19 wherein the alkylcarbonyl is valeroly.

22. The method of claim 19 wherein the alkylcarbonyl is heptanoyl.

* * * * *